United States Patent [19]
Jones et al.

[11] Patent Number: 5,190,058
[45] Date of Patent: Mar. 2, 1993

[54] METHOD OF USING A TEMPORARY STENT CATHETER

[75] Inventors: Lee A. Jones, Minneapolis; Leanne Dittmer, Fridley; Rodney G. Wolff, Maple Grove; Vincent Hull, Fridley, all of Minn.

[73] Assignee: Medtronic, Inc., Minneapolis, Minn.

[21] Appl. No.: 703,975

[22] Filed: May 22, 1991

[51] Int. Cl.$^5$ ............................................. A61M 29/02
[52] U.S. Cl. .................................... 128/898; 606/194; 606/198
[58] Field of Search ............... 606/192, 194, 191, 198; 128/898

[56] References Cited

U.S. PATENT DOCUMENTS

| | | | |
|---|---|---|---|
| 4,572,186 | 2/1986 | Gould et al. | 604/104 X |
| 4,585,000 | 4/1986 | Hershenson . | |
| 4,612,931 | 9/1986 | Dormia . | |
| 4,650,466 | 3/1987 | Luther . | |
| 4,733,665 | 3/1988 | Palmaz . | |
| 4,776,337 | 10/1988 | Palmaz . | |
| 4,885,003 | 12/1989 | Hillstead . | |
| 4,921,484 | 5/1990 | Hillstead . | |
| 4,998,539 | 3/1991 | Delsanti | 128/898 |
| 5,002,531 | 3/1991 | Bonzel . | |
| 5,002,560 | 3/1991 | Machold et al. . | |
| 5,034,001 | 7/1991 | Garrison et al. | 604/53 |

FOREIGN PATENT DOCUMENTS 0321912 12/1988 European Pat. Off. .

Primary Examiner—Michael H. Thaler
Attorney, Agent, or Firm—Daniel W. Latham; Harold R. Patton

[57] ABSTRACT

A temporary stent catheter and method for use. The catheter is particularly useful for restoring patency to an artery following a Percutaneous Transluminal Coronary Angioplasty (PTCA) procedure. The catheter comprises a catheter tube having a distal end and a proximal end; an elongated balloon inflatable by fluid pressure attached to the catheter tube near its distal end; a stent having a generally tubular configuration attached to the catheter tube near its distal end and surrounding the balloon; a pressurization device near the proximal end of the catheter tube for inflating and deflating the balloon whereby the stent may be pressed against the wall of a blood vessel by the balloon and the balloon may be subsequently deflated to permit blood flow through the expanded stent; and a restriction device near the proximal end of the catheter tube for maintaining the stent in an expanded condition and for subsequently effecting the radial contraction of the stent whereby it may be removed from the blood vessel.

6 Claims, 3 Drawing Sheets

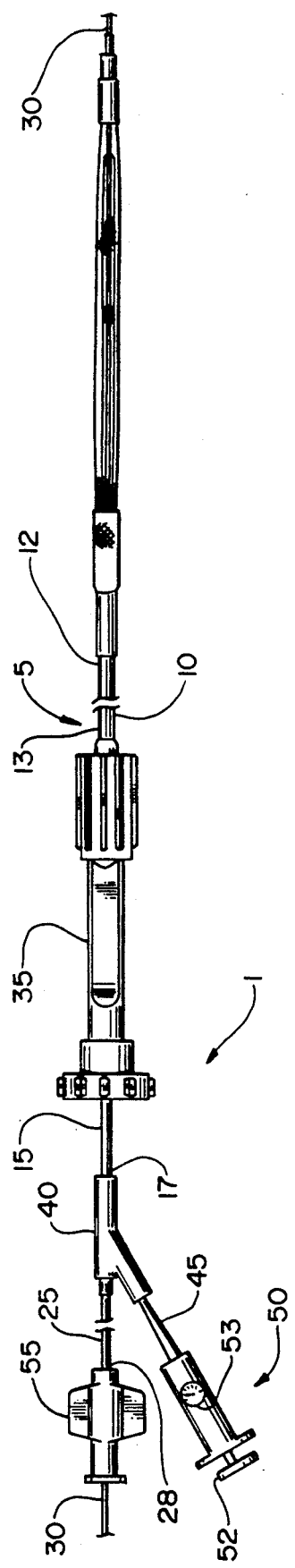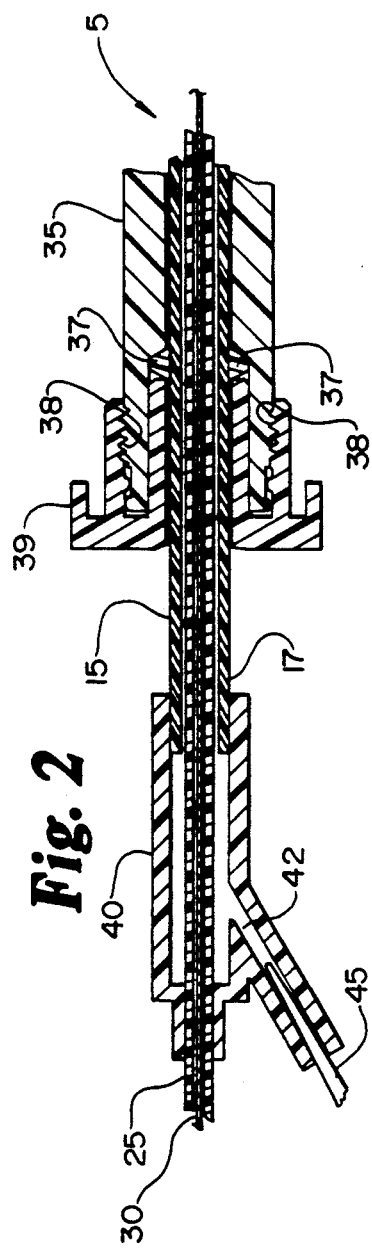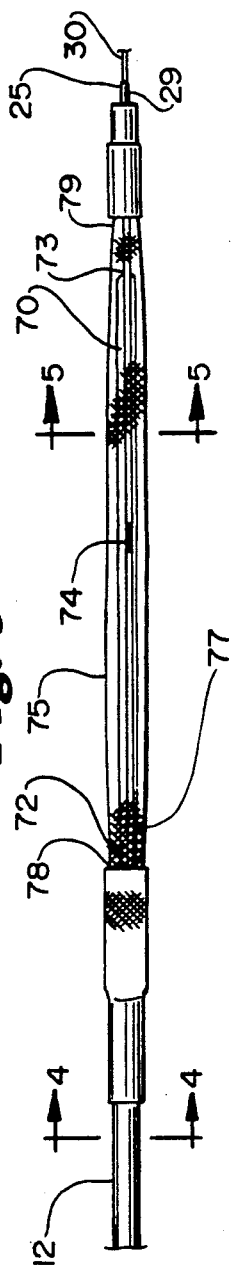

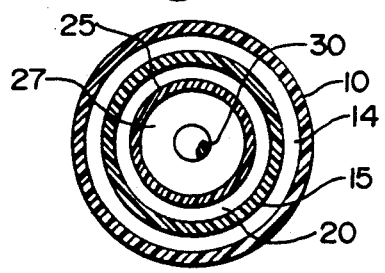
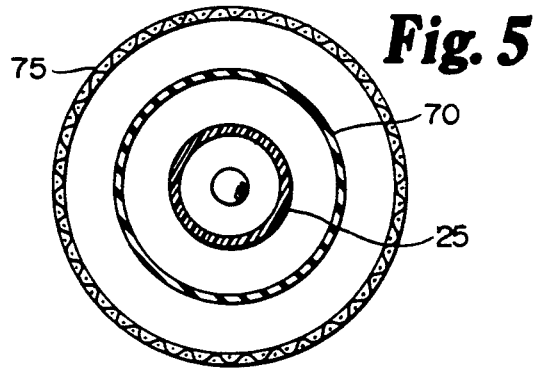
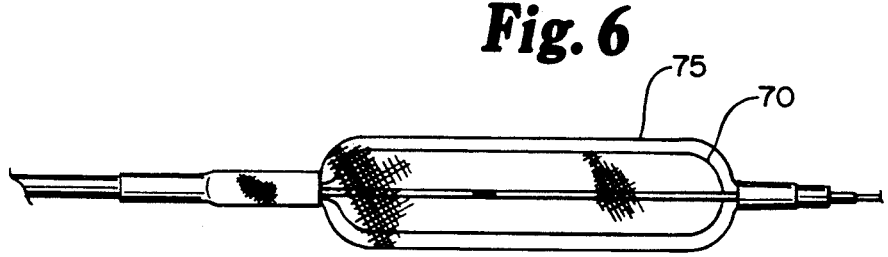
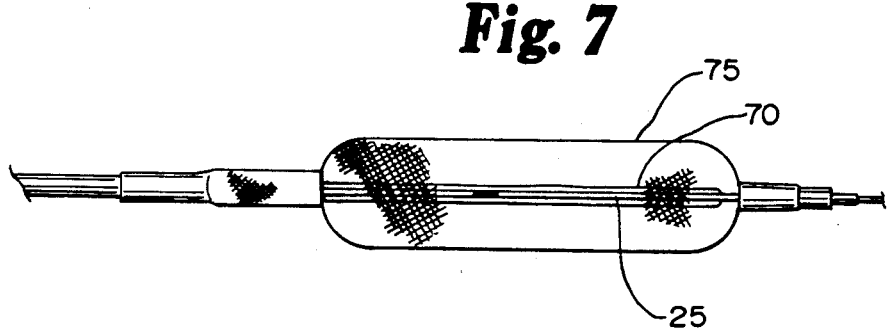

METHOD OF USING A TEMPORARY STENT CATHETER

BACKGROUND OF THE INVENTION

This invention relates to a temporary stent catheter for use within a body passageway or duct and more particularly to the use of a temporary stent for restoration of patency to arterial lesions following Percutaneous Transluminal Coronary Angioplasty (PTCA).

PTCA is an increasingly accepted treatment for persons suffering from coronary artery disease. However, it does have several disadvantages, one of which is that of acute closure of the coronary artery following the PTCA procedure. By "acute closure" we mean a sudden blockage of blood flow in the coronary artery at the lesion site addressed by the PTCA procedure. This closure is believed to be initiated by cracks, fissures and flaps appearing at the lesion site following the PTCA procedure. In approximately 5–10% of all PTCA procedures, the dissected flaps will either occlude or threaten to occlude the artery. If left untreated, the occlusion can result in ischemia or myocardial infarction.

It has been shown that if these flaps can be pressed against the artery wall for a period of time, they will adhere to the artery wall and the acute or threatened closure will be relieved. PTCA balloon catheters are commonly used in an effort to press the flaps against the artery wall. However, the use of a balloon has the significant disadvantage that the balloon itself occludes the artery being treated and therefore cannot remain inflated in the artery for the period of time necessary to restore patency to the artery.

Reperfusion devices have been developed to press flaps against the artery wall while permitting blood to flow through the artery. For example, the Stack perfusion catheter is an angioplasty balloon that has a lumen through which blood can flow. Also, for example, U.S. Pat. No. 4,585,000 to Hershenson employs a mechanically expanding device provided with a passageway to permit blood flow through the device. However, these devices have the disadvantage that the passageways through the device are small and blood flow can be occluded during prolonged use.

Yet another device for reperfusion is the "Gaspard" catheter in which a braided mesh near the end of a catheter is mechanically expanded to press the flaps against the artery wall. This device permits greater treatment duration since blood is able to flow through the mesh. Similar devices are shown in U.S. Pat. Nos. 4,650,466 to Luther and 4,921,484 to Hillstead. However, these devices generally lack the mechanical strength afforded by a balloon system.

It is therefore an object of the present invention to provide a temporary stent capable of being inserted in a body passageway or duct, expanded to support the passageway or duct, and subsequently removed.

It is also an object of the present invention to provide a temporary stent that will permit the flow of fluids through the portion of the duct or passageway being treated.

It is also an object of the present invention to provide a temporary stent capable of pressing occluding flaps appearing following a PTCA procedure against the arterial wall to restore patency of the artery.

SUMMARY OF THE INVENTION

These and other objects are accomplished by the temporary stent catheter of the present invention. We have discovered that a temporary stent catheter can be made comprising a catheter tube having a distal end and a proximal end; an elongated balloon inflatable by fluid pressure attached to the catheter tube near its distal end; a stent having a generally tubular configuration attached to the catheter tube near its distal end and surrounding the balloon; means near the proximal end of the catheter tube for inflating and deflating the balloon whereby the stent may be pressed against the wall of a blood vessel by the balloon and the balloon may be subsequently deflated to permit blood flow through the stent; and means near the proximal end of the catheter tube for maintaining the stent in an expanded condition and for subsequently effecting the radial contraction of the stent whereby it may be removed from the blood vessel.

In a preferred embodiment of the invention, the temporary stent catheter has a catheter tube with multiple tube elements, for example, a first tube having a distal end and a proximal end and a passageway therethrough extending from the distal end to the proximal end; and a second, fluid-tight tube slidably located within the passageway of the first tube and having a proximal end extending beyond the proximal end of said first tube and having a distal end extending to the distal end of the first tube and having a passageway extending from the proximal end to the distal end. The catheter tube is completed by an elongated element which preferably is a tube through which a guide wire can be introduced, the elongated element attached in a fixed position within the passageway of the second tube and having a proximal end extending beyond the proximal end of the second tube. An elongated balloon inflatable by fluid pressure is positioned around the distal end of the elongated element and in communication with the passageway of the second, fluid-tight tube. A stent of interlaced filaments forms a tubular mesh around the balloon and has a proximal end attached near the distal end of the first tube and a distal end attached to the elongated element near a distal end of the elongated element. A means for applying and releasing fluid pressure is also present, for example in the form of a conventional manual plunger-type device capable of maintaining or releasing applied pressure, at the proximal end of the fluid-tight tube and in communication with the passageway of the fluid-tight tube.

In operation, the catheter is first inserted into the body duct or passageway (such as a blood vessel) to be supported. The balloon is then inflated causing the stent to expand and press radially against the wall of the blood vessel. Following the expansion step, the movement of the first tube is restricted with respect to the second tube, thus locking the stent in a radially expanded position. The balloon is then deflated by reduction in pressure, thus permitting blood to flow through the stent. Restoring the sliding action between the first and second tubes allows the second tube and elongated element to move with respect to the first tube which unlocks the stent and allows it to radially contract when the support of the stent is no longer needed. The movement of the second tube and elongated element allows the resilient mesh of the stent to move axially which necessarily causes it to contract radially to its normal position. Once the stent is radially contracted away from the walls of the blood vessel, the temporary stent catheter may be removed from the blood vessel.

BRIEF DESCRIPTION OF THE DRAWINGS

FIG. 1 is a plan view of one embodiment of the temporary stent catheter of the present invention.

FIG. 2 is a cross sectional view in side elevation of a proximal portion of the catheter of FIG. 1 including a valve and a "Y" fitting.

FIG. 3 is a side elevational view of a distal portion of the catheter of FIG. 1 including the mesh and balloon portions.

FIG. 4 is a sectional view taken along line 4—4 of FIG. 3.

FIG. 5 is a sectional view taken along line 5—5 of FIG. 3.

FIG. 6 is a side elevational view of the catheter of FIG. 3 in which the balloon portion of the catheter has been inflated causing the mesh to expand.

FIG. 7 is a side elevational view of the catheter of FIG. 6 in which the balloon portion of the catheter has been deflated but the mesh remains expanded.

FIG. 8 is a side elevational view of the catheter of FIG. 7 in which the mesh has been radially contracted.

DETAILED DESCRIPTION OF THE INVENTION

Figure 9:
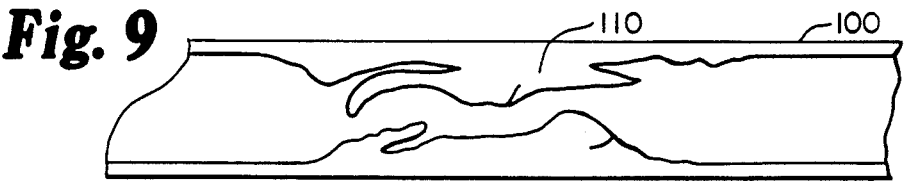
FIG. 9 is a cross sectional view in side elevation of a blood vessel having a portion with flaps, cracks and dissections threatening closure.

The temporary stent catheter of the present invention is intended to be a stent permanently attached to a catheter for temporary use to support a body duct or passageway. Its primary application is in the repair of lesions following PTCA procedures or to maintain patency of a blood vessel until surgery can be undertaken although it can be of value in other applications where a body duct or passageway must be temporarily supported without interrupting the flow of body fluids through the duct or passageway. When the application of the stent is completed, it is radially contracted and withdrawn intact from the body duct or passageway.

In general, the temporary stent catheter has as major elements a catheter tube, an elongated balloon inflatable by fluid pressure, and a stent having a generally tubular configuration. The catheter tube has at least one fluid-tight passageway extending from its proximal to its distal end to supply fluid pressure from a pressurization device at its proximal end to the balloon located near its distal end. The catheter also requires means for maintaining the stent in a radially expanded condition and for radially contracting the stent once the procedure is completed. This is preferably accomplished by a simple mechanical connection between the stent and the user of the device operating through the catheter tube. Also preferably, the catheter tube provides a passageway for a conventional guide wire such that the distal end of the catheter can be guided into a desired position in the body duct or passageway. Generally, materials suitable for use in the catheter tube are well known to those skilled in the art since they are substantially the same materials conventionally used in PTCA devices and other medical catheters.

The catheter includes an elongated balloon inflatable by fluid pressure attached near the distal end of the catheter tube. The balloon can be of a conventional configuration and materials such as the polyethylene balloons used in PTCA catheters. In order to provide adequate pressure to expand the stent portion of the catheter, a balloon capable of withstanding at least 1 to 2 atmospheres of pressure should be used. Conventional pressures for PTCA procedures of 6 to 8 atmospheres may also be used if desired. In an alternative embodiment, an elastic balloon could be used which would completely deflate on the catheter tube, thus providing no balloon "wings" on the catheter tube when deflated by application of vacuum. In any case, the balloon should have a low profile design to allow blood to flow around it when it has been deflated.

The catheter also includes a stent having a generally tubular configuration attached to the catheter tube near its distal end and surrounding the balloon. The stent fits snugly over the catheter tube and over the balloon and except for attachments at its proximal and distal ends, the stent is generally allowed to move freely with respect to the balloon. The stent has supporting elements which provide an open structure when the stent is expanded into contact with the wall of the body duct or passageway such that body fluids in the duct or passageway may pass through the stent and continue downstream along the duct or passageway. A wire mesh stent with a braided configuration and fewer filaments to interrupt blood flow is preferred. The stent must also have a configuration which allows it to be radially collapsed or contracted so that it can be removed following completion of the procedure. The material used in the stent is preferably a resilient material such as stainless steel which may be altered in radial strength by heat treating as desired or such as polyethylene teraphthalate (PET). A readily deformable material such as tantalum could also be used advantageously in the present invention since it would conform to the shape of the artery to be treated better than a resilient material. The stent and other components of the catheter can be secured to the catheter tube by means well known in the catheter art such as by the use of melting, swaging, shrink tubing or adhesives.

The catheter also has means near the proximal end of the catheter tube which allows the user to inflate and deflate the balloon. As described above, a simple, manually operable pressurization device can be used for both inflation by application of appropriate amounts of pressure and by deflation by application of vacuum or subatmospheric pressure.

The catheter also has means near the proximal end of the catheter tube for both maintaining the stent in a radially expanded condition during the procedure and for effecting the radial contraction of the stent so that it may be removed from the blood vessel. As described above, this can be accomplished by the use of a simple mechanical connection between the stent and the user operating through the catheter tube.

In operation, the catheter is first inserted into the body duct or passageway (such as a blood vessel) to be supported. The balloon is then inflated causing the stent to expand and press radially against the wall of the blood vessel. Generally, pressures above one atmosphere of pressure are required to press the stent into place although, depending on the stent used, pressures as high as 6 to 8 atmospheres may be required. Following the expansion step, the stent is locked in a radially expanded position. If the stent is made from a resilient material, this can be accomplished by applying and maintaining an axial compressive force on the stent which forces it to maintain its radially expanded position. If the stent is made from a deformable material, locking of the stent in the radially expanded position is accomplished by the deformation of the stent material as it is brought into contact with the wall of the blood vessel. The balloon is then deflated by reduction in pressure, thus permitting blood to flow through the stent. The stent is then unlocked and allowed to radially contract when the support of the stent is no longer needed. In stents made from a resilient material, an axial force extending the stent may optionally be applied to assist in the radial contraction of the stent. In stents made from a deformable material, an axial force which extends the stent is usually required to unlock and radially contract the stent. Once the stent is radially contracted away from the walls of the blood vessel, the temporary stent catheter may be removed from the blood vessel.

Although it will be recognized by those skilled in the art that there are many possible embodiments of the present invention, the invention will be described in detail according to the following embodiment.

Referring now to FIGS. 1, 2 and 4, in an embodiment of the invention, the temporary stent catheter has a catheter tube 5 with multiple tube elements, for example, a first tube 10 having a distal end 12 and a proximal end 13 and a passageway 14 therethrough extending from the distal end 12 to the proximal end 13; and a second, fluid-tight tube 15 slidably located within the passageway 14 of the first tube 10 and having a proximal end 17 extending beyond the proximal end 13 of said first tube 10 and having a distal end (not shown) near the distal end 12 of the first tube 10 and having a passageway 20 extending from the proximal end 17 to the distal end (not shown). The catheter tube 5 also has an elongated element 25 which preferably is a tube having a passageway 27 through which a guide wire 30 can be introduced, the elongated element 25 attached in a fixed position within the passageway 20 of the second tube 15 and having a proximal end 28 extending beyond the proximal end 17 of the second tube 15.

The catheter tube assembly also comprises a number of additional elements. At the proximal end 13 of the first tube 10, the first tube 10 is secured to a restriction device 35. The second tube 15 runs through the restriction device 35, past a closely fitting resilient washer 37. The restriction device 35 also includes a threaded portion 38 and a threaded cap 39. In operation, the threaded cap 39 is tightened onto the resilient washer 37, causing the resilient washer 37 to pinch the second tube 15 such that the second tube 15 is held immobile in the restriction device 35 and cannot slide within the passageway 14 of the first tube 10. The restriction device 35 must not, however, completely block the passageway 20 of the second tube 15. At the proximal end 17 of the second tube 15, is a "Y" connection 40 which is secured to the second tube 15. The elongated element 25 and guide wire 30 pass through the "Y" connection 40 uninterrupted. A tube element 45 is also attached to the "Y" connection 40 and is connected at its other end to a pressurization device 50. Optionally, a connector (not shown) may be placed in the tube element 45 between the pressurization device 50 and the "Y" connection 40 to allow the pressurization device 50 to be removed for reuse. The "Y" connection 40 has a passageway 42 which communicates with the passageway 20 of the second tube 15 such that fluid pressure from the pressurization device 50 can be transmitted through the passageway 20 of the second tube 15. Also shown is a fitting 55 at the proximal end 28 of the elongated element 25 through which the guide wire 30 may be operated.

The pressurization device 50 is of conventional design having a plunger handle 52 through which pressure may be applied and released, a locking mechanism (not shown) allowing the user to hold a desired pressure and a pressure gauge 53 allowing the user to apply a desired amount of pressure. Preferably the working fluid is a substantially incompressible fluid such as is used in conventional PTCA devices.

Referring also now to FIGS. 3, 4 and 5, an elongated balloon 70 inflatable by fluid pressure is positioned at the distal end 29 of the elongated element 25 and secured at a distal end 73 to the elongated element 25 and also secured at a proximal end 72 to the second tube 15 in communication with the passageway 20 of the second tube 15. Radiopaque material is applied in a band 74 as a demarcation of the center of the useable area for the balloon 70.

A stent 75 of interlaced filaments 77 forms a tubular mesh around the balloon 70 and has a proximal end 78 attached near the distal end 12 of the first tube 10 and a distal end 79 attached to the elongated element 25 near a distal end 29 of the element 25. The filaments 77 of the tubular mesh comprise a resilient material such as stainless steel.

Referring also to FIGS. 6-8, in operation, the stent 75 and the balloon 70 initially lie substantially flat with respect to the elongated element 25. The restriction device 35 is first loosened to allow the second tube 15 to slide axially with respect to the first tube 10. The balloon is then inflated by pressing on the plunger handle 52 of the pressurization device 50 causing fluid pressure to be transmitted along the passageway 20 of the second tube 15 to the balloon 70. The inflation causes the balloon 70 to press against the stent 75 causing the stent 75 to expand radially. The restriction device 35 is then tightened to prevent relative movement of the first tube 10 and the second tube 15. The balloon 70 is then deflated by pulling on the plunger 52 to apply vacuum until the balloon 70 again lies against the elongated element 25. The stent 75 is maintained in an expanded configuration due to the axial compression of the stent 75 maintained by the restriction device 35. When the stent 75 is to be radially contracted, the restriction device 35 is first released. The sliding action between the second tube 15 and the first tube 10 then allows the second tube 15 and elongated element 25 to move at a proximal end 17 with respect to the first tube 10 to effect the radial contraction. The advancement of the second tube 15 and elongated element 25 allows the mesh (made from a resilient material) to move axially to its original position which necessarily causes it to contract radially.

Figure 10:
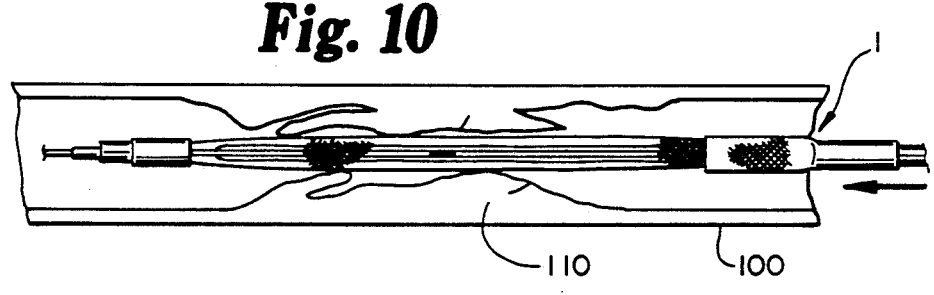
FIG. 10 is a side elevational view of the catheter of FIG. 3 inserted into the blood vessel of FIG. 10.
Figure 11:
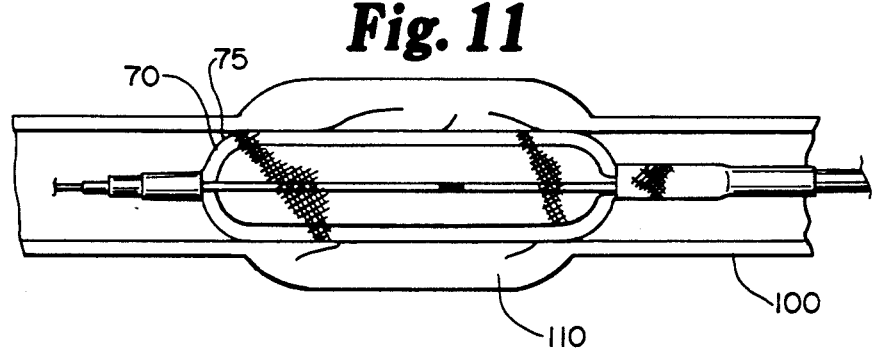
FIG. 11 is a side elevational view of the catheter and blood vessel of FIG. 10 in which the balloon portion has been inflated causing the mesh to expand within the blood vessel.
Figure 12:
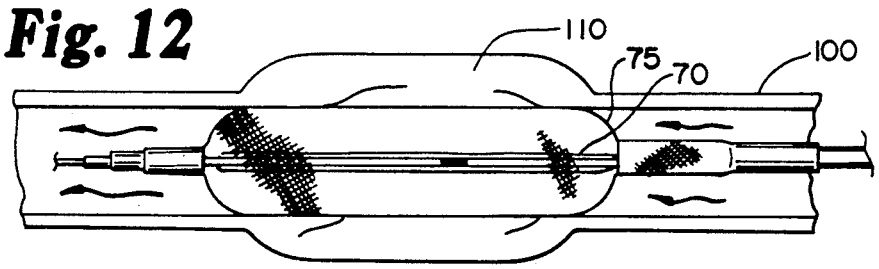
FIG. 12 is a side elevational view of the catheter and blood vessel of FIG. 11 in which the balloon portion has been deflated while the mesh remains expanded.
Figure 13:
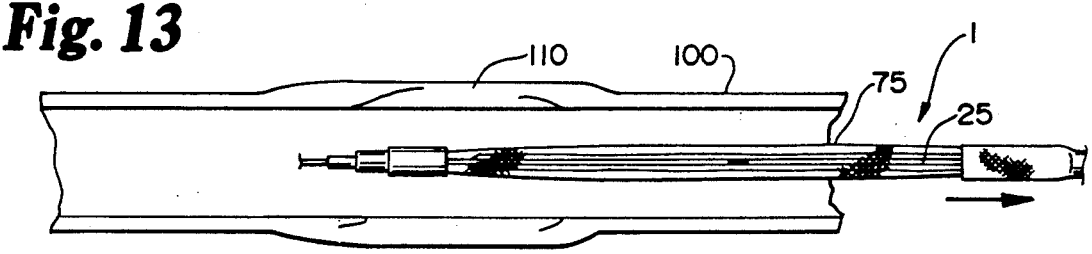
FIG. 13 is a side elevational view of the catheter and blood vessel of FIG. 12 in which the mesh portion has been radially contracted and is being removed from the blood vessel.

Referring now also to FIGS. 9-13, to treat an arterial lesion using the device of the present invention, the catheter is first conventionally introduced into the artery 100 and guided to the lesion 110 by use of the radiopaque marker 74. The stent 75 and the balloon 70 initially lie substantially flat with respect to the elongated element 25 as the stent 75 is introduced into the lesion 110. The restriction device 35 is loosened to allow the second tube 15 to slide axially with respect to the first tube 10. The balloon is then inflated by pressing on the plunger handle 52 of the pressurization device 50 causing fluid pressure to be transmitted along the passageway 20 of the second tube 15 to the balloon 70. The inflation causes the balloon 70 to press against the stent 75 causing the stent 75 to expand radially into contact with the lesion 110 and compress the lesion 110. The restriction device 35 is then tightened to prevent relative movement of the first tube 10 and the second tube 15 thus locking the stent 75 in its radially expanded position. The balloon 70 is then deflated by pulling on the plunger 52 to apply vacuum until the balloon 70 again lies against the elongated element 25. The stent 75 remains expanded against the lesion 110. Blood may then flow in the artery 100 through the mesh of the stent 75. The stent remains in place for a period of time needed to adhere any flaps to the artery 100 which may be minutes or even hours. When the stent 75 is to be removed, the restriction device 35 is first released to unlock the stent 75. The sliding action between the second tube 15 and the first tube 10 is thereby restored which then allows the second tube 15 and elongated element 25 to move at a proximal end 17 with respect to the first tube 10 to effect the radial contraction of the stent 75. The advancement of the second tube 15 and elongated element 25 allows the mesh (made from a resilient material) to move axially to its original position which necessarily causes it to contract radially. The catheter 1 can then be removed from the artery 100.

It will be appreciated by those skilled in the art that not all of the elements of the multi-tube catheter are strictly necessary for the construction of a device according to the present invention. For example, only one tube and an elongated element could be used in combination to provide the necessary mechanical movement and applied pressure needed to operate such a device.

The additional tube used in the exemplary embodiment above merely avoids the issue of providing sealing for high pressure fluids in elements which must also be able to move with respect to each other. It will also be appreciated that in an embodiment using a deformable stent element, radially contracting the stent would require an application of mechanical force to stretch the mesh axially and thereby contract it radially.

Also, while the invention has been described above in connection with particular embodiments, one skilled in the art will appreciate that the invention is not necessarily so limited and that numerous other embodiments, examples, uses and modifications of and departures from the embodiments, examples and uses may be made without departing from the inventive concepts.

We claim:

1. A method for providing temporary support for a blood vessel comprising the steps of:
   (a) inserting into the blood vessel a catheter having at a distal end a balloon and a stent;
   (b) inflating the balloon in the blood vessel to cause the stent to expand radially and press against the blood vessel;
   (c) locking a restriction device onto the catheter, thereby immobilizing the expanded stent in the radially expanded position;
   (d) deflating the balloon to allow blood to flow through the locked stent;
   (e) unlocking the restriction device and radially contracting the stent to disengage the stent from the blood vessel;
   (f) removing the catheter and stent from the blood vessel.

2. The method of claim 1 wherein the balloon is inflated by at least one atmosphere of pressure.

3. The method of claim 1 wherein the stent is locked by maintaining the stent in axial compression.

4. The method of claim 1 wherein the stent is locked by deformation of the stent into the radially expanded position.

5. The method of claim 3 wherein the stent is unlocked by releasing axial compression.

6. The method of claim 3, 4 or 5 wherein the stent is radially contracted by axially extending the stent.

* * * * *